United States Patent [19]
Murchie

[11] Patent Number: 5,868,131
[45] Date of Patent: Feb. 9, 1999

[54] BABY'S BREATHING AID

[76] Inventor: Barry Joseph Murchie, 62 Oxley Drive, Bowral, NSW 2576, Australia

[21] Appl. No.: 793,671
[22] PCT Filed: Sep. 1, 1995
[86] PCT No.: PCT/AU95/00580
  § 371 Date: Feb. 28, 1997
  § 102(e) Date: Feb. 28, 1997
[87] PCT Pub. No.: WO96/07391
  PCT Pub. Date: Mar. 14, 1996

[30] Foreign Application Priority Data

Sep. 2, 1994 [AU] Australia .................... PM7848

[51] Int. Cl.⁶ .................. A61M 15/00; A61M 16/00; A62B 7/00; A61J 17/00
[52] U.S. Cl. ................. 128/204.13; 128/202.13; 606/234
[58] Field of Search ............... 128/200.24, 203.12, 128/203.21, 204.11, 204.13, 207.14, 202.13; 606/234; 424/435

[56] References Cited

U.S. PATENT DOCUMENTS

| | | | |
|---|---|---|---|
| 165,799 | 7/1875 | Daniels | 128/204.13 |
| 4,520,809 | 6/1985 | de Greef et al. | 128/207.18 |
| 4,669,461 | 6/1987 | Battaglia et al. | 128/207.18 |
| 4,959,051 | 9/1990 | Glass et al. | 606/234 |
| 5,013,321 | 5/1991 | MacVane | 606/234 |
| 5,123,915 | 6/1992 | Miller et al. | 606/234 |
| 5,176,705 | 1/1993 | Noble | 606/234 |
| 5,300,024 | 4/1994 | Yang | 606/234 |
| 5,354,274 | 10/1994 | Demeter et al. | 606/234 |
| 5,395,392 | 3/1995 | Suhonen | 606/234 |

FOREIGN PATENT DOCUMENTS

| | | | |
|---|---|---|---|
| 406505 | 1/1991 | European Pat. Off. | |
| 1120990 | 7/1956 | France | 606/234 |
| 3820291 | 12/1989 | Germany | |
| 296422 | 12/1991 | Germany | |
| 337983 | 6/1959 | Switzerland | 128/204.13 |
| 679009 | 12/1991 | Switzerland | |
| 1757682 | 8/1992 | U.S.S.R. | 128/203.12 |
| 566742 | 1/1945 | United Kingdom | 606/234 |
| 2231497 | 11/1990 | United Kingdom | |
| 2269754 | 2/1994 | United Kingdom | |

OTHER PUBLICATIONS

Abstract of Patent No. ZA 8801–564–A, Nov. 1988.

*Primary Examiner*—Kimberly L. Asher
*Attorney, Agent, or Firm*—Dinsmore & Shohl LLP

[57] ABSTRACT

An infant breathing aid assembly comprising an infant soother having a safety shield with at least one vent cooperates with a decongestant module having a housing for housing vapor emitting medicine and fixing means adapted to be retentively received in the vent for fixing the housing to the infant soother. In use the housing closely abuts the safety shield to substantially seal the vapor emitting medicine within the housing and the safety shield, and the housing emits vapor from the medicine.

11 Claims, 5 Drawing Sheets

BABY'S BREATHING AID

This Application is a 371 application PCT/AU95/0580 filed 01 Sep. 1995.

BACKGROUND OF INVENTION

This invention relates to a method and apparatus for assisting the breathing of an infant suffering from minor ailments such as breathing and nasal congestion problems and the like due to, for example, a cold.

The invention also has application in the dispensing of therapeutic oils which may also assist in alleviating sleeping, coughing and relaxation problems in infants.

DESCRIPTION OF PRIOR ART

There are many known methods of treating an infant for breathing difficulties and the like. These include the application of decongestants, nose droppers, and vapor emitting ointments. However parents often desire to avoid the overuse of medicines such as decongestants and droppers. Vaporising ointments are somewhat messy if applied to the skin of the baby and some babies are allergic to chemicals in ointments. Ointments also tend to collect small particles such as dirt and dust on the child and/or clothing.

It is known for a decongestant to be associated with a baby's pacifier. Examples of known arrangements are to be found in UK patents 2231497 and 2269754 to Singh, EP patent 406505 to Doll and CH patent 679009 to Naf.

SUMMARY OF INVENTION

The present invention aims to provide an alternative to known infant breathing aids.

In one aspect this invention resides broadly in a replaceable vapor dispensing module for attachment to an infant soother having a safety shield to thereby constitute an infant breathing aid assembly, the vapor dispensing module including:

a housing for housing a vapor emitting medicine and/or therapeutic oil, and fixing means for fixing the housing to the infant soother;

wherein in use the housing closely abuts the safety shield to substantially seal the vapor emitting medicine and/or therapeutic oil within the housing and the safety shield, the housing being adapted to emit vapor from medicine housed therewithin and the arrangement being such that the replaceable vapor dispensing module is adapted to cooperate with infant soothers having differently shaped safety shields.

As used herein the expression "replaceable" means that a vapor dispensing module can be replaced on an infant soother without also replacing the infant soother per se.

As used herein the expression "infant soother" means a teat or teat-simulating device for placing in an infant's mouth on which the infant suckles. An infant soother is also known as a dummy or a pacifier.

The fixing means can fix the module to the pacifier in different ways. For example the fixing means may be received in receiving means such as a recess on the pacifier for retentively receiving the module in a snap fit action. However it is preferred that the fixing means is adapted to be received in a vent in the safety shield.

The housing may be customised to fit individual types of soothers however it is preferred that the housing is adapted to closely abut differently shaped safety shields. The housing may be a flexible shell.

It is preferred that the fixing means includes spigot means. In one embodiment the spigot means includes a pair of resilient fingers fixed to the housing. Alternatively, the spigot means can be lockingly engageable in a recess in the housing. It is preferred that the vapor emitting medicine and/or therapeutic oil is carried in a carrier.

In another aspect this invention resides broadly in an infant breathing aid assembly including:

an infant soother having a safety shield and anchor means for anchoring a vapor dispensing module thereto, and a replaceable vapor dispensing module having a housing for housing a vapor emitting medicine and/or therapeutic oil and fixing means for fixing the housing to the anchor means;

wherein in use the housing closely abuts the safety shield to substantially seal the vapor emitting medicine and/or therapeutic oil within the housing and the safety shield, the housing being adapted to emit vapor from medicine housed therewithin and the arrangement being such that the replaceable vapor dispensing module is adapted to cooperate with infant soothers having differently shaped safety shields.

In a preferred embodiment the anchor means includes at least one vent in the safety shield. Alternatively the anchor means can include receiving means for retentively receiving the vapor dispensing module in a snap fit action. In another embodiment the anchor means can comprises handle means on the infant soother and the medicine may be suitably packaged for attachment to the handle means.

Preferably the vapor dispensing module is located on the soother in a position to avoid direct contact between the medicine and the baby's face. The housing may include passage means such as perforations or it can be in the form of a cage or the like to facilitate travel of the vapor from the medicine to the baby.

The components of the breathing aid may be of any suitable material, and may be formed, for example, by plastics moulding.

In a further aspect this invention resides broadly in a method of treating breathing difficulties and nasal congestion in infants, the method including:

fitting a vapor dispensing module as defined above to an infant soother, whereby in use, when the soother is in the infant's mouth, the infant can inhale medicinal vapor emitted from the module.

In yet another aspect this invention resides broadly in an infant breathing aid assembly including:

an infant soother having a safety shield and a handle attached to the soother for anchoring a vapor dispensing module thereto, and a replaceable vapor dispensing module including a housing for housing a vapor emitting medicine and/or therapeutic oil, and fixing means for fixing the housing to the infant soother;

wherein in use the fixing means cooperates with the handle and the vapor emitting medicine and/or therapeutic oil is substantially sealed within the housing, the housing being adapted to emit vapor from medicine and/or therapeutic oil housed therewithin and the arrangement being such that the replaceable vapor dispensing module is adapted for use with differently shaped infant soothers.

BRIEF DESCRIPTION OF DRAWINGS

In order that the invention may be more readily understood and put into practical effect, reference will now be made to the accompanying drawings which illustrate preferred embodiments of the invention, wherein.

DETAILED DESCRIPTION OF INVENTION

Figure 1:
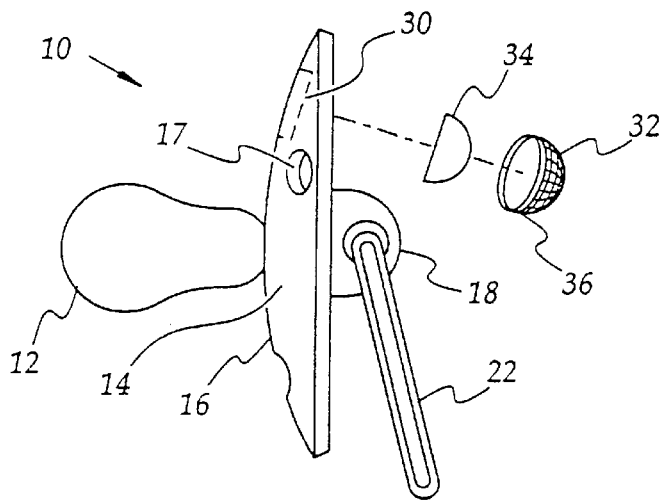
FIG. 1 is a side view of an infant's breathing aid constructed in accordance with this invention.
Figure 2:
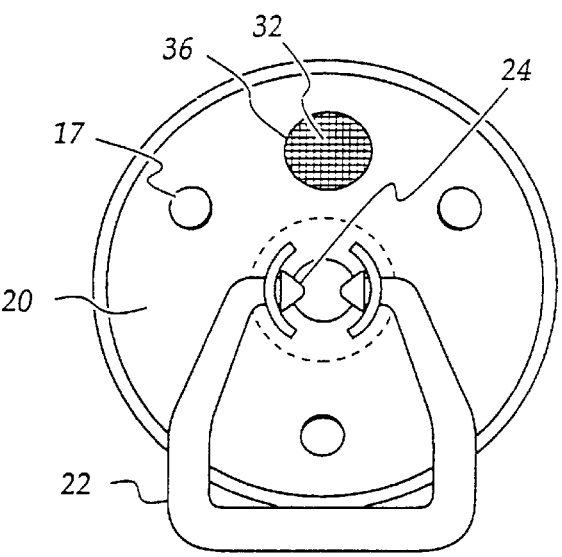
FIG. 2 is a rear view of the breathing aid shown in FIG. 1.
Figure 3:
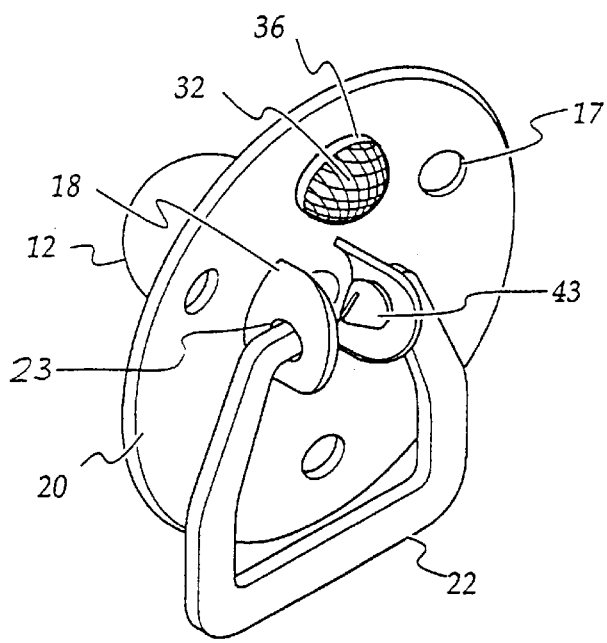
FIG. 3 is a perspective rear view of the breathing aid shown in FIGS. 1 and 2, and FIGS. 4 to 7, FIGS. 8 to 10, FIGS. 11 to 14 and FIG. 15 respectively illustrate alternative embodiments of the invention.
Figure 4:
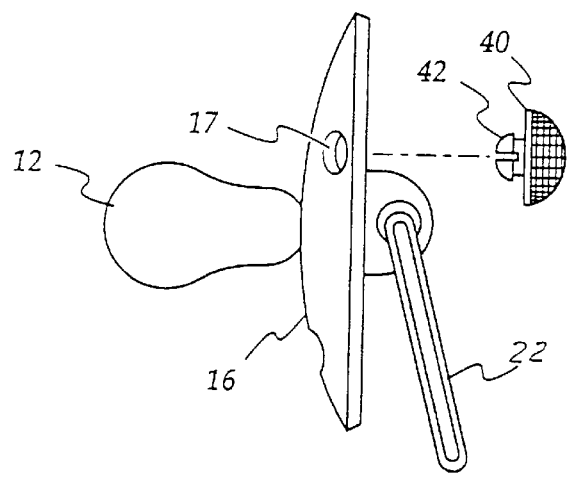
Figure 5:
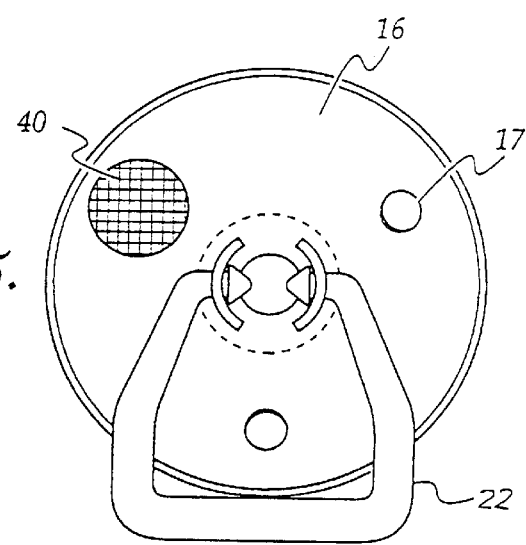
Figure 6:
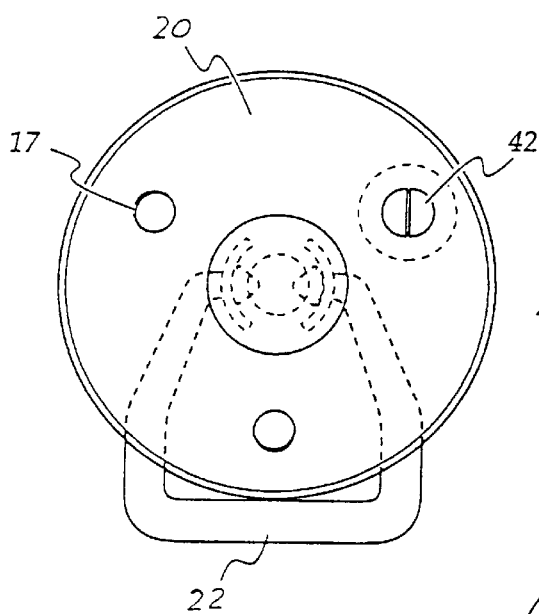
Figure 7:
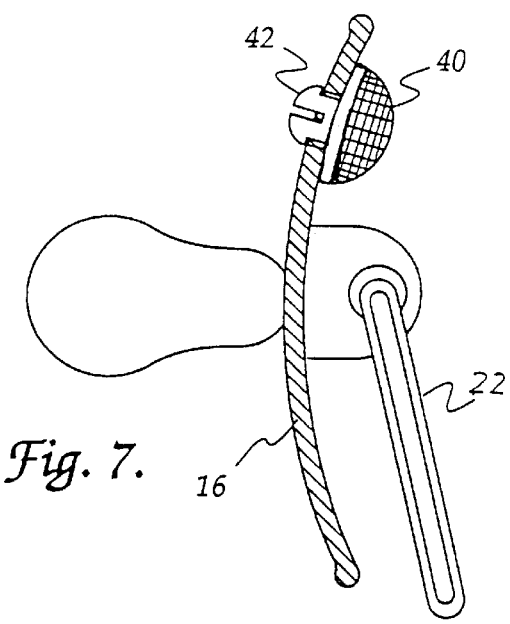

Referring to FIGS. 1 to 3, a known standard infant soother 10 is provided with a rubber teat 12 which is attached to the front face 14 of a face or safety shield 16. The face shield may be convex relative to the teat as shown, or it may be flat or concave. Three angularly spaced ventilation apertures 17 extend through the face shield. A handle mounting 18 is integrally moulded to the rear face 20 of the face shield 16, and a U shaped handle 22 is pivotally received in a pair of aligned apertures 23 provided in the handle mounting 18. The ends 24 of the handle 22 are attached to the handle mounting apertures 23 in a releasable snap action arrangement.

The rear face 20 of shield 16 has a vapor dispensing module receiving (or anchor) means in the form of a circular recess 30 adapted to receive a vapor dispensing module having a flexible housing in the form of a cage 32 which houses a replaceable pad 34 of absorbent material. Both the pad 34 and the cage 32 are hemispherical in shape and the cage 32 is releasably retained in the recess 30 by a snap action fit with the recess and the base rim 36 of the cage. It will be appreciated that the flexible cage 32 can also fit to a convex surface of a shield.

In operation, a vapor emitting medicine and/or therapeutic oil is applied to the absorbent pad 34 and the pad and cage assembly is snap fitted into engagement with the circular recess 30 in the rear face 20 of the face shield 16. The vapor fumes travel towards the baby's face via the ventilating apertures 17 and/or via the periphery of the face shield 16. As the pad and cage assembly is readily releasable, the absorbent pad 34 may be re-impregnated with the vapor emitting medicine and/or therapeutic oil when desired or alternatively, replaced with a new pad.

The snap action fit of the cage 32 with the rim 36 of the cage 32 and the snap action fit of the handle ends 24 with the apertures 23 of the handle mounting, avoid release by a young child.

Referring to FIGS. 4 to 7 an alternative vapor dispensing module differs from that shown in FIGS. 1 to 3 in that a flexible housing in the form of cage 40 is provided with a plug 42 having a pair of resilient fingers. Plug 42 releasably snap fits into one of the ventilating apertures 17.

Figure 8:
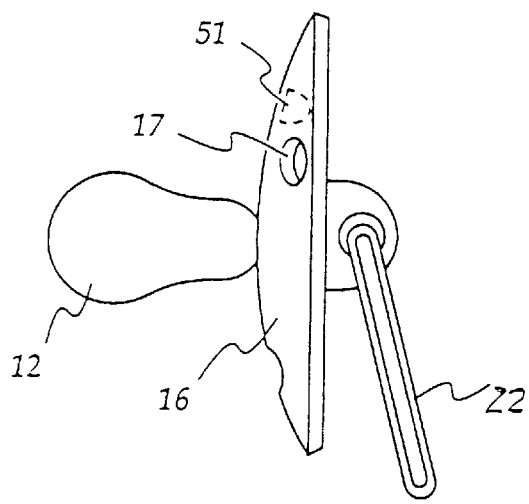
Figure 9:
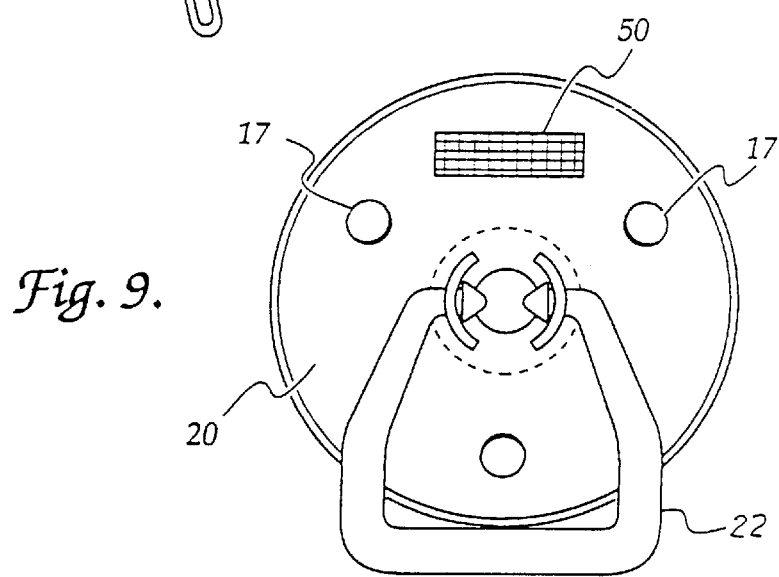
Figure 10:
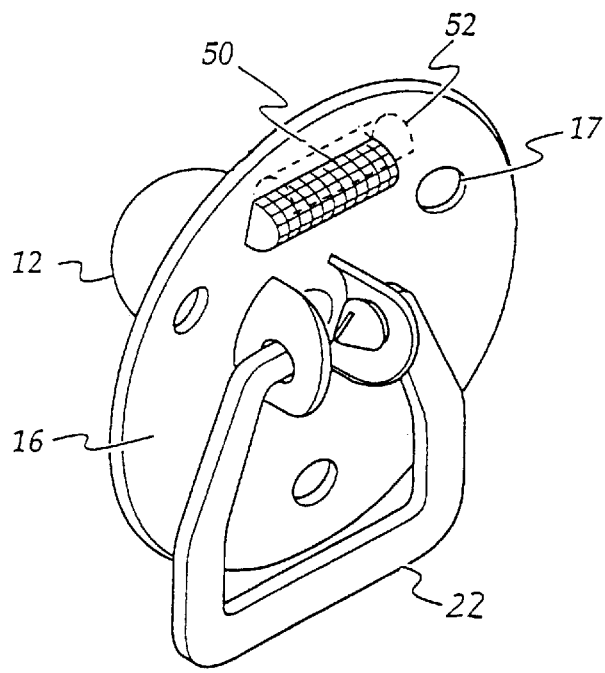
Figure 11:
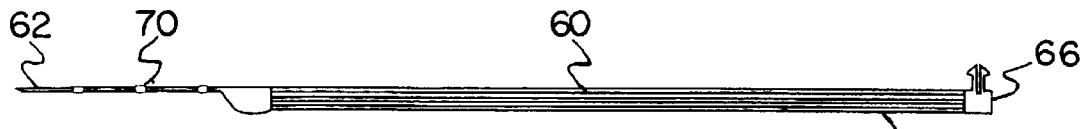
Figure 12:
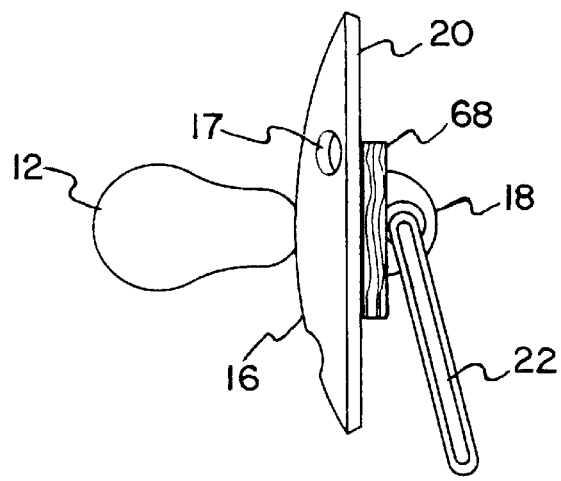
Figure 13:
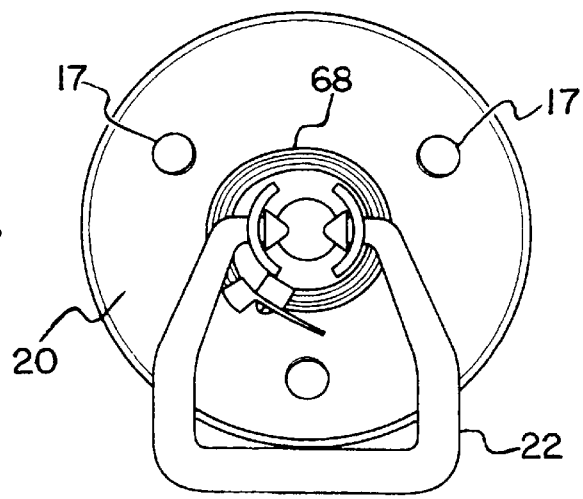
Figure 14:
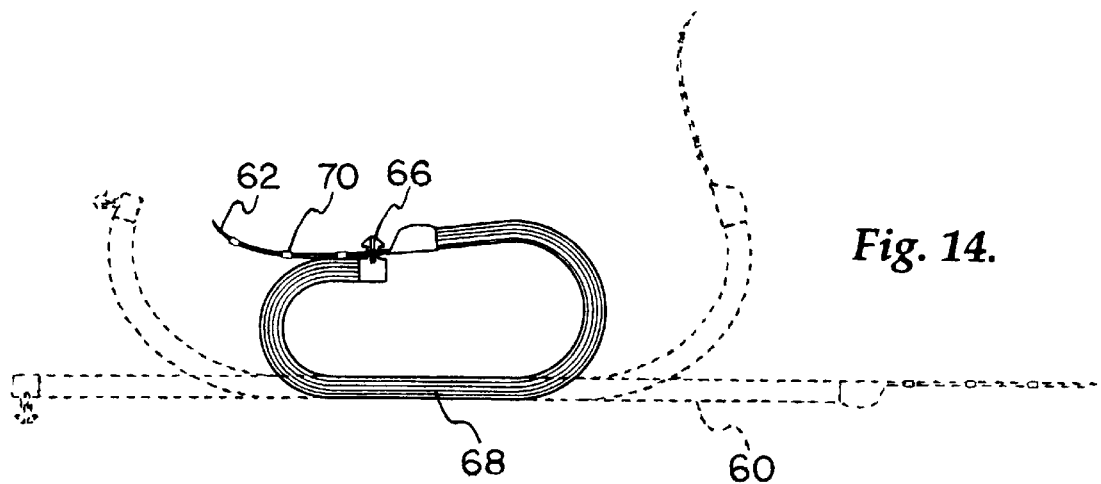

Referring to FIGS. 8 to 10 an alternative vapor dispensing module differs from that shown in FIGS. 1 to 3 in that an elongated cage 50 is received in a recess 51 in the rear face 20 of the shield. The cage is located adjacent two ventilating apertures 17 and is provided with a pivotal retaining cover 52. The cover 52 can be locked into position by a suitable snap action arrangement.

Referring to FIGS. 11 to 14 a vapor dispensing module is in the form of a band 60 of absorbent material which is retained in position adjacent the rear face 20 of the face shield 16 by the handle 22. The two ends 62 and 64 of the band (shown in dotted outline in FIG. 14) are connected together by fastening means such as a plug and rivet 66 to form a conveniently sized ring 68. One end 62 of the band is provided with spaced adjustment apertures 70 to facilitate selection of different sized rings. The ends of the bands may be locked into place to avoid accidental separation. An alternative arrangement is to manufacture the band in the form of a non-adjustable standard sized ring whereby the ring can be located in position or replaced by removing and subsequently replacing the snap action fitted handle 22.

Figure 15:
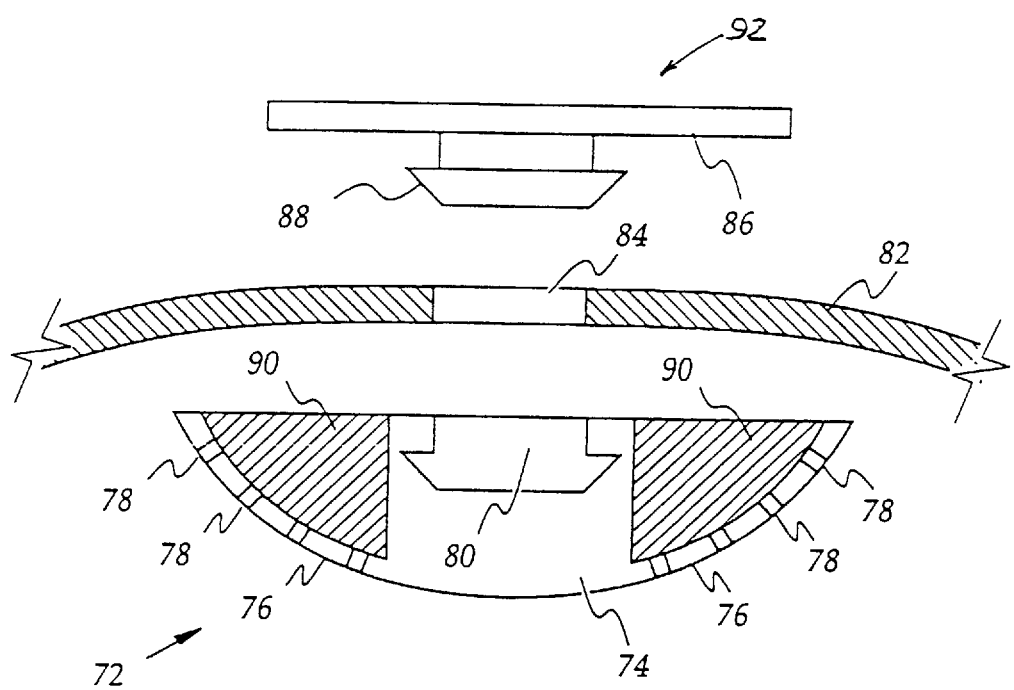

Alternatively as seen in FIG. 15, a vapor dispensing module 72 has a central boss 74 about which a flexible mushroom-like skirt 76 depends. Skirt 76 has apertures 78 through which vapor escapes from a medicine impregnated pad 90 housed in skirt 76. Module 72 is mounted to a soother by being located in vent 84 of shield 82 by means of plug 92 having an upper flange 86 which abuts against the opposite side of shield 82 when spigot 88 is received in a matching recess 80 in boss 74. Such an arrangement is less likely to be detached by a more mature infant. Other child proof fitting arrangements can be used.

The embodiments of the invention have a number of advantages over the prior art devices known to the applicant in that the chemicals of the medicine should not come into contact with the skin during normal use, messy applications of ointments to the skin are avoided and the pacifying action of the soother should help to relax the child. The breathing aid may also be used as a conventional soother/pacifier.

Moreover the vapor dispensing module of the present invention is adapted for use with standard soothers irrespective of the configuration of the safety shield. The replaceable modules also enable an infant to retain a favorite soother when the vapor dispensing module itself has been exhausted of medicine because the module can be replaced rather than the complete soother having to be discarded.

It will also be appreciated that the replaceable modules can be purchased separately from the pacifiers. This enables modules containing pharmaceutical vapor emitting medicines such as decongestants, which are available only if prescribed by a medical practitioner, to be separately packaged and purchased independently of a soother or of any particular type of soother.

It will of course be realised that whilst the above has been given by way of illustrative examples of this invention, all such and other modifications and variations hereto, as would be apparent to persons skilled in the art, are deemed to fall within the broad scope and ambit of this invention as is hereinafter claimed.

I claim:

1. A replaceable vapor dispensing module for attachment to an infant soother having a safety shield, said vapor dispensing module including:

a housing for containing a vapor emitting medicine and/or therapeutic oil, said housing adapted to emit vapor from said medicine and/or oil, and fixing means adapted to fix said housing to an infant soother such that said housing will closely abut the safety shield of the infant soother for substantially sealing a vapor emitting medicine and/or therapeutic oil between said housing and the safety shield;

wherein said housing is flexible and thereby adapted to cooperate with infant soothers having differently shaped safety shields.

2. A vapor dispensing module as claimed in claim 1, wherein said fixing means is adapted to be received in a vent in the safety shield.

3. A vapor dispensing module as claimed in claim 2, wherein said housing is a flexible shell.

4. A vapor dispensing module as claimed in claim 2, wherein said fixing means includes spigot means.

5. A vapor dispensing module as claimed in claim 4, wherein said spigot means includes a pair of resilient fingers.

6. A vapor dispensing module as claimed in claim 4, wherein said spigot means is lockingly engageable in a recess in said housing.

7. A vapor dispensing module as claimed in claim 1, wherein said vapor emitting medicine and/or therapeutic oil is carried in a carrier.

8. An infant breathing aid assembly including:
an infant soother having a safety shield and anchor means for anchoring a vapor dispensing module thereto, and
a replaceable vapor dispensing module attached to said infant soother, said vapor dispensing module including a housing for containing a vapor emitting medicine and/or therapeutic oil, said housing adapted to emit vapor from said medicine and/or oil, and fixing means adapted to fix said housing to said infant soother such that said housing closely abuts said safety shield of the infant soother for substantially sealing a vapor emitting medicine and/or therapeutic oil between said housing and said safety shield;
wherein said housing is flexible and thereby adapted to cooperate with infant soothers having differently shaped safety shields.

9. An infant breathing aid assembly as claimed in claim 8, wherein said anchor means includes receiving means for retentively receiving said vapor dispensing module in a snap fit action.

10. An infant breathing aid assembly as claimed in claim 8, wherein said anchor means comprises handle means on said infant soother.

11. An infant breathing aid assembly including:
an infant soother having a safety shield and anchor means or anchoring a vapor dispensing module thereto, and
a vapor dispensing module having a flexible housing for containing vapor emitting medicine and/or therapeutic oil, said flexible housing adapted to emit vapor from said medicine and/or oil, and fixing means cooperable with said anchor means for fixing said housing to said infant soother such that said flexible housing closely abuts said safety shield so that the vapor emitting medicine and/or theapeutic oil will be substantially sealed between said housing and said safety shield,
wherein said anchor means includes at least one vent in said safety shield.

* * * * *

UNITED STATES PATENT AND TRADEMARK OFFICE
CERTIFICATE OF CORRECTION

PATENT NO. : 5,868,131
DATED : February 9, 1999
INVENTOR(S) : Barry Joseph Murchie It is certified that error appears in the above-identified patent and that said Letters Patent is hereby corrected as shown below:

Claim 11, column 6, line 13, replace "or" with --for--.

Claim 11, column 6, line 21, replace "theapeutic" with --therapeutic--.

Signed and Sealed this

Twenty-fifth Day of May, 1999

Attest:

Q. TODD DICKINSON

*Attesting Officer*     Acting Commissioner of Patents and Trademarks